(12) United States Patent
Magdassi et al.

(10) Patent No.: US 9,095,133 B2
(45) Date of Patent: Aug. 4, 2015

(54) PESTICIDE NANOPARTICLES OBTAINED FROM MICROEMULSIONS AND NANOEMULSIONS

(75) Inventors: Shlomo Magdassi, Jerusalem (IL); Benny Dayan, Rehovot (IL); Ganit Levi-Ruso, Beer Sheva (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 626 days.

(21) Appl. No.: 12/441,321

(22) PCT Filed: Sep. 16, 2007

(86) PCT No.: PCT/IL2007/001137
§ 371 (c)(1),
(2), (4) Date: Sep. 15, 2009

(87) PCT Pub. No.: WO2008/032328
PCT Pub. Date: Mar. 20, 2008

(65) Prior Publication Data
US 2010/0015236 A1    Jan. 21, 2010

Related U.S. Application Data

(60) Provisional application No. 60/844,366, filed on Sep. 14, 2006.

(51) Int. Cl.
*A01N 25/04* (2006.01)
*A01N 25/14* (2006.01)
*A01N 47/34* (2006.01)
*A01N 53/00* (2006.01)

(52) U.S. Cl.
CPC ............... *A01N 25/14* (2013.01); *A01N 25/04* (2013.01); *A01N 47/34* (2013.01); *A01N 53/00* (2013.01)

(58) Field of Classification Search
None
See application file for complete search history.

(56) References Cited

U.S. PATENT DOCUMENTS

| 4,073,943 | A | 2/1978 | Wretlind et al. |
| 4,534,891 | A | 8/1985 | Boden .................... 252/999.999 |
| 4,725,442 | A | 2/1988 | Haynes ........................ 424/490 |
| 5,032,585 | A | 7/1991 | Lichtenberger |
| 5,091,187 | A | 2/1992 | Haynes ........................ 424/450 |

(Continued)

FOREIGN PATENT DOCUMENTS

| EP | 211 257 | 2/1987 |
| EP | 0760237 | 3/1997 |

(Continued)

OTHER PUBLICATIONS

NPIC fact sheet, "Lambda-cyhalothrin" (2001).*

(Continued)

*Primary Examiner* — Bethany Barham
*Assistant Examiner* — Barbara Frazier
(74) *Attorney, Agent, or Firm* — Winston & Strawn LLP

(57) ABSTRACT

The present invention provides a redispersible powder and aqueous dispersions of nanoparticles of water insoluble organic pesticides. The invention further provides methods for preparing the redispersible powder and the aqueous dispersion, wherein the methods include preparation of an oil-in-water nanoemulsion or microemulsion and solvent removal. The present invention also provides pesticidal compositions of the redispersible powder or aqueous dispersions, and their agricultural use in combating pests.

20 Claims, 1 Drawing Sheet

(56) References Cited

U.S. PATENT DOCUMENTS

| | | | |
|---|---|---|---|
| 5,091,188 A | 2/1992 | Haynes | 424/450 |
| 5,112,688 A | 5/1992 | Michael | 428/402.2 |
| 5,134,129 A | 7/1992 | Lichtenberger | |
| 5,145,684 A * | 9/1992 | Liversidge et al. | 424/489 |
| 5,145,842 A | 9/1992 | Driedger | 514/63 |
| 5,183,746 A | 2/1993 | Shaked et al. | |
| 5,250,236 A | 10/1993 | Gasco | 264/4.4 |
| 5,260,284 A | 11/1993 | Lichtenberger | |
| 5,346,542 A | 9/1994 | Yosuke et al. | |
| 5,472,706 A | 12/1995 | Friedman et al. | 424/450 |
| 5,512,092 A | 4/1996 | Maruyama et al. | |
| 5,560,930 A | 10/1996 | Maruyama et al. | |
| 5,560,933 A | 10/1996 | Soon-Shiong et al. | |
| 5,750,142 A | 5/1998 | Friedman et al. | 420/450 |
| 5,767,112 A | 6/1998 | Poli et al. | |
| 5,874,029 A | 2/1999 | Subramaniam et al. | |
| 5,879,715 A | 3/1999 | Higgins et al. | |
| 5,891,469 A | 4/1999 | Amselem | |
| 5,916,596 A | 6/1999 | Desai et al. | |
| 6,255,253 B1 | 7/2001 | Foerster et al. | 504/363 |
| 6,265,180 B1 * | 7/2001 | Zuelli et al. | 435/29 |
| 6,589,548 B1 | 7/2003 | Oh et al. | |
| 6,706,863 B2 | 3/2004 | Hashimoto | 534/742 |
| 6,770,722 B2 | 8/2004 | Weitzel et al. | 526/331 |
| 6,835,396 B2 | 12/2004 | Brynjelsen et al. | 424/450 |
| 6,841,595 B2 | 1/2005 | Brizzolara et al. | 524/2 |
| 6,841,613 B1 | 1/2005 | Taisne et al. | 524/549 |
| 6,872,773 B2 | 3/2005 | Pakusch et al. | 524/560 |
| 6,893,493 B2 | 5/2005 | Cho et al. | |
| 2004/0131691 A1 | 7/2004 | Casson | 424/489 |
| 2005/0031692 A1 | 2/2005 | Beyerinck et al. | |
| 2005/0170004 A1 | 8/2005 | Rosenberger et al. | 424/490 |
| 2005/0281884 A1 | 12/2005 | Adair et al. | |
| 2006/0025358 A1 | 2/2006 | Marshall | |
| 2006/0063676 A1 | 3/2006 | Brigance et al. | 504/116.1 |
| 2006/0165742 A1 | 7/2006 | Reizlein | |

FOREIGN PATENT DOCUMENTS

| | | |
|---|---|---|
| WO | WO 01/88046 A2 | 11/2001 |
| WO | WO 2005/020933 A2 | 3/2005 |
| WO | WO 2005/072709 A2 | 8/2005 |
| WO | 2005/087002 | 9/2005 |
| WO | WO 2005/102507 A1 | 11/2005 |
| WO | 2006/000671 | 1/2006 |
| WO | 2007/048730 | 5/2007 |
| WO | 2008/006712 | 1/2008 |
| WO | WO 2008/032327 | 3/2008 |

OTHER PUBLICATIONS

International Search Report PCT/IL07/01136 Dated Mar. 3, 2008.
International Search Report PCT/IL07/01137 Dated Sep. 9, 2008.
Debuigne, F. et al., (2000) Synthesis of monodisperse nimesulide nanoparticles in microemulsions E170/isopropyl myristate/water/n-butanol (or isopropanol). *J. Pharm Belg.* 55(2):59-60.
Debuigne, F. et al. (2000) Synthesis of Organic Nanoparticles in Different W/O Microemulsions. *Langmuir* 16(20):7605-7611.
Desgouilles, Stephanie et al., (2003) The design of nanoparticles obtained by solvent evaporation: a comprehensive study. *Langmuir* 19(22):9504-9510.
Dowler, Clyde C. et al., (1999) Polymeric Microcapsules of Alachlor and Metolachlor: Preparation and Evaluation of Controlled-Release Properties. *J Agric Food Chem.* 47, 2908-2913.
Hsu, Chang-Hsuan et al., (2003) Preparation and characterization of novel coenzyme Q10 nanoparticles engineered from microemulsion precursors. *AAPS PharmSciTech* 4(3):E32.
Magdassi, Shlomo and Moshe, Matti Ben (2003) Patterning of Organic Nanoparticles by Ink-jet Printing of Microemulsions. *Langmuir* 19(3):939-942.
Ozer, F. et al. (2000) Methacrylate-based nanoparticles produced by microemulsion polymerization. *J. App. Poly. Sci.* 78(3):569-575.
Perez-Martinez, Jose et al., (2001) Ethyl cellulose polymer microspheres for controlled release of norfluazon. Pest Manag Sci 57(8):688-694.
Trotta, Michele et al., (2003) Preparation of griseofulvin nanoparticles from water-dilutable microemulsions. *Int. J. Pharm.* 254(2):235-242.
Yoncheva, K. et al. (2003) Influence of process parameters of high-pressure emulsification method on the properties of pilocarpine-loaded nanoparticles. *J. Microencapsul.* 20(4):449-458.
Aouak, Taieb et al., (2000) Microemulsion breakdown by pervaporation technique: the cyclohexane/water/$n$-butanol/sodium dodecylsulfate system. Journal of Membrane Science 173:149-157.
Aranberri, Ibon et al., (2002) How Do Emulsions Evaporate? *Langmuir* 18(9):3471-3475.
Biais, J. et al., (1982) Thermodynamic properties of microemulsions: Pseudophase equilibrium-vapor pressure measurements. Journal of Colloid and Interface Science 86(2):350-358.
Damaszewski, Leona and Mackay, Raymond A. (1984) Equilibrium vapor pressure in microemulsions: a test of the pseudophase model. Journal of Colloid and Interface Science 97(1):166-175.
Friberg, Stig E. et al., (1995) Evaporation from a microemulsion in the water-Aerosol OT-cyclohexanone system. Colloids and Surfaces A: Physicochemical and Engineering Aspects 100:83-92.
Jeunieu, L. et al., (Ed) (2001) Synthesis of inorganic and organic nanoparticles in microemulsions. pp. 609-631 in: Reactions and Synthesis in Surfactant Systems. CRC Press.
Landfester, Katharina and Ramirez, Liliana P. (2003) Encapsulated magnetite particles for biomedical. *J. Phys. Condens. Matter* 15:S1345-S1361.
Marchand, K. E. et al., (2003) Investigation of AOT-based microemulsions for the controlled synthesis of MoSx nanoparticles : an electron microscopy study. Colloids and Surfaces A: Physicochem. Eng. Aspects 214:239-248.
Monnoyer, Ph. et al., (1995) Preparation of colloidal AgBr particles from microemulsions. Colloids and Surfaces A: Physicochemical and Engineering Aspects 100:233-243.
O'Donnell, Patrick B. And McGinity, J. W. (1997) Preparation of microspheres by the solvent evaporation technique. Advanced Drug Delivery Reviews 28(1):25-42.
Reigart, J. Routt and Roberts, James R. (1999) Recognition and Management of Pesticide Poisonings. Fifth edition US Environmental Protection Agency Available on the internet at: http://www.epa.gov/pesticides/safety/healthcare/.
Tan, Hock S. and Pfister, Wiliam R. (1999) Pressure-sensitive adhesives for transdermal drug delivery systems. *Pharm Sci and Tech Today* 2(2):60-69.
Texter, John (Ed) (2001) Organic particle precipitation. pp. 577-607 in: Reactions and Synthesis in Surfactant Systems. CRC Press.
U.S. Appl. No. 12/441,308 Requirement for Restriction/Election Jan. 11, 2012.
U.S. Appl. No. 12/441,308 Non-Fianl Rejection Apr. 9, 2012.
Rosca et al., (2004) Microparticle formation and its mechanism in single and double emulsion solvent evaporation. J Control Release 99(2): 271-280.
Chen et al., (2000) Studies on cloud point of agrochemical microemulsions. Colloids and Surfaces A: Physicochemical and Engineering Aspects 175(1-2): 257-262.

* cited by examiner

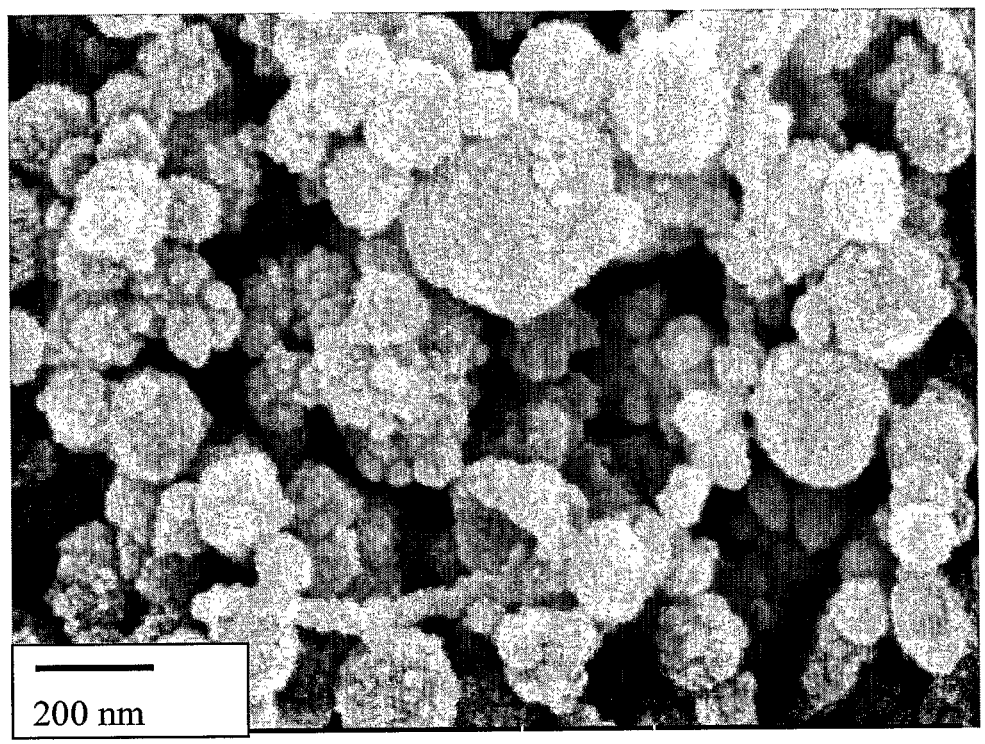

PESTICIDE NANOPARTICLES OBTAINED FROM MICROEMULSIONS AND NANOEMULSIONS

This application is a 371 filing of International Patent Application PCT/IL2007/001137 filed Sep. 16, 2007, which claims the benefit of application No. 60/844,366 filed Sep. 14, 2006.

FIELD OF THE INVENTION

The present invention relates to nanoparticles of a water-insoluble organic compound in the form of a redispersible powder or aqueous dispersion, and a process for the production of such nanoparticles from microemulsions and nanoemulsions.

BACKGROUND OF THE INVENTION

Many chemical compounds are substantially insoluble in water. There are several different approaches to solve the solubility problem of poorly water-soluble chemical compounds. These include traditional solubilizing approaches using a combination of solvents, surfactants and co-solvents, various dispersion techniques, as well as micronization, complexation and liposomal delivery techniques.

Dissolution of active agents in solvents is an approach which is used both for delivery of pesticides into plant crops and for preparation of water-immiscible drugs for in vivo delivery. This approach becomes problematic for pesticides which, unlike pharmaceutical agents used in low concentrations, require relatively high concentrations of active agent for pest control, and accordingly large amounts of solvents for dissolution. Typically, the solvents used are not environmentally acceptable and pose potential health and safety risks to handlers. Further, the handler is exposed to toxic and/or irritant levels of pesticides while manipulating the materials during the dissolution. Hence, some current methods of agrochemical formulation and delivery are disadvantageous, as they are environmentally "unfriendly" and expose handlers to excessive levels of pesticides and solvents.

Current technology for delivering insoluble agents (as described in, e.g., U.S. Pat. Nos. 5,091,188; 5,091,187 and 4,725,442) involves either coating small active agent particles with surface active substances or dissolving the drug in a suitable lipophilic carrier and forming a stabilized emulsion. For many of these processes, emulsions are the starting point employed to achieve small particle size of poorly water-soluble agents using a hydrophobic solvent (e.g., oil) and a stabilized mechanism within an aqueous medium. One of the problems of these formulations is that certain particles in suspension tend to grow over time because of the "Oswald ripening" phenomenon. Another problem is that many insoluble agents of interest do not show appreciable solubility within traditional oil emulsion systems. One reason for this is that solubility is not strictly defined by polarity, but also includes hydrogen bonding, dipole-dipole interactions, ionic stabilization and atom-to-atom interactions.

Another approach directed to delivery and release of poorly soluble chemical compounds includes their formulation as nano-sized particles (nanoparticles). Nanoparticles of organic compounds can be produced through the use of microemulsions, comprising either water-in-oil "reverse" microemulsions, or oil-in-water microemulsions. Nanoparticles prepared from water-in-oil microemulsions have been disclosed with respect to each of cholesterol, Rhovanil and Rhodiarome (Debuigne et al. *Langmuir* 2000, 16(20), 7605-7611), and nimesulide (Debuigne et al. *J. Pharm Belg.* 2000 55(2), 59-60).

Nanoparticles prepared by methods comprising solvent diffusion (not solvent evaporation) from oil-in-water microemulsions have been disclosed with respect to griseofulvin, an antifungal drug (Trotta M., et al. *Int. J. Pharm.* 2003, 245, 235-242). Latex nanoparticles can also be obtained by polymerization (not solvent evaporation) in oil-in-water microemulsion (Ozer et al. *J. App. Poly. Sci.* 2000, 78(3), 569-575). Solid lipid microspheres can be prepared by solidification (not solvent evaporation) from oil-in-water microemulsion (U.S. Pat. No. 5,250,236). Pigment nanoparticles can be produced from oil-in-water microemulsion in ink-jet printing processes by evaporation of volatile solvent on a substrate surface (Magdassi and Ben Moshe *Langmuir* 2003, 19(3), 939-942).

Nanoparticles obtained using emulsion (not microemulsion) and solvent evaporation techniques have been disclosed with respect to cellulose derivatives and polylactic acid (Desgouilles et al. *Langmuir* 2003, 19, 9504-9510); and pilocarpine encapsulated within poly(lactide-co-glycolide) polymer (Yoncheva et al. *J. Microencapsul.* 2003, 20(4), 449-458).

WO 2005/072709 discloses a drug delivery system comprising nanoparticles of a water poorly soluble drug dispersed in a polymeric hydrophilic bead, and a method for producing the drug delivery system. The disclosed method comprises mixing an oil-in-water submicron emulsion comprising a poorly water soluble drug, with a water-soluble bead forming polymer; providing conditions enabling bead formation; optionally evaporating volatile organic solvent and water used in earlier steps, and thereby obtaining dry beads containing dispersed nanoparticles of the poorly water soluble drug.

WO 2005/102507 describes a process for preparing nanoparticles from oil-in-water nanoemulsions, in which the nanoemulsion is prepared by phase inversion, or temperature inversion techniques.

WO 2005/020933 relates to a process for the preparation of polymeric nanoparticles with target molecules bonded to the surface of the particles and having sizes of up to 1000 nm, preferably 1 nm to 400 nm, more preferably 1 nm to 200 nm that are dispersed homogeneously in aqueous solution. The polymeric nanoparticles are prepared using emulsion polymerization technique.

WO 01/88046 describes a process to pattern organic nanoparticles by ink-jet printing of microemulsions.

U.S. Pat. No. 5,091,188 discloses injectable formulations of water-insoluble drugs as aqueous suspensions of phospholipid-coated microcrystals, wherein the drug is reduced to 50 nm to 10 μm dimensions by sonication or other high shear processes in the presence of phospholipid or another membrane-forming amphipathic lipid.

U.S. Pat. No. 4,725,442 discloses preparation by sonication of microdroplets of water-insoluble drugs coated with phospholipids, wherein the microdroplets are from about 200 Angstroms up to one micron in diameter.

U.S. Pat. No. 5,879,715 relates to a process for the production of inorganic nanoparticles by precipitating the inorganic nanoparticles by a precipitating agent from a microemulsion with a continuous and a non-continuous phase and concentrating the precipitated nanoparticles employing an ultra filtration membrane.

U.S. Pat. No. 5,874,029 describes the production of microparticles and nanoparticles in which a compressed fluid and a solution including a solvent and a solute are introduced into a nozzle to produce a mixture. The mixture is then passed out of the nozzle to produce a spray of atomized droplets. The atomized droplets are contacted with a supercritical antisolvent to cause depletion of the solvent in the droplets so that the particles are produced from the solute. Preferably, these particles have an average diameter of 0.6 μm or less. This process relies on a spraying type vaporization process.

US Patent Application No. 2005/0170004 relates to nanoparticles comprising an organic wax and a surfactant, wherein a peptide, polysaccharide or glycoprotein is electrostatically attached to the nanoparticle. Hsu et al. (*AAPS Pharm Sci Tech* 2003, 4(3), E32) relates to nanoparticles of encapsulated coenzyme Q10 in lyophilized and aqueous suspension forms, and their production from microemulsions.

Preparation of Water-Redispersible Powders and Water-Wettable Polymeric Powders has also been disclosed. U.S. Pat. Nos. 5,472,706 and 5,750,142 disclose a lyophilized composition comprising submicron particles and an amino compound cryoprotectant, and a method of making a lyophilized composition, wherein the method involves use of a submicron oil-in-water emulsion comprising an amino compound cryoprotectant. European Patent No. 211257 relates to lyophilized emulsion compositions comprising carbohydrates which are intended for parenteral administration of hydrophobic drugs.

U.S. Pat. No. 6,835,396 discloses a process for preparing submicron sized particles of a pharmacologically active compound by forming a crude dispersion in a water immiscible solvent and a surfactant, subjecting the crude dispersion to sonication in order to form a fine dispersion, freezing the fine dispersion, and lyophilizing the frozen dispersion to obtain particles having a diameter less than 500 nm.

U.S. Pat. No. 6,872,773 discloses preparation of a powder by spray-drying of an aqueous dispersion of polymer particles. U.S. Pat. No. 6,841,613 discloses water re-dispersible granules obtainable by drying an emulsion obtained by polymerizing. Other powder forming processes comprise a polymerization step, such as disclosed for example in U.S. Pat. No. 6,841,595 relating to the preparation of protective colloid-stabilized, emulsifier-free, aqueous dispersions based on at least two monomers, and U.S. Pat. No. 6,770,722 relating to the preparation of protective-colloid-stabilized polymers by continuous emulsion polymerization.

As outlined above, prior art nanoparticle formulations intended for delivery of water-insoluble organic compounds comprise encapsulating materials and/or special ingredients and techniques required for maintaining the final material in powder or dispersed form. Such formulations and methods suffer from increased production time and costs, and more complicated regulatory approval processes.

U.S. Patent Application No. 2006/0063676 relates to a transparent stable aqueous oil-in-water microemulsion of an agrochemical and a surface active agent as emulsifier, wherein 50% of the droplets of the microemulsion have a size in the range from 100 to 300 nm.

Dowler et al. (J. Agric. Food Chem. 1999, 47, 2908-2913) relate to use of emulsification using the solvent dichlomethane and the polymer ethyl cellulose for the preparation of microcapsules for preparation of controlled release formulations of the herbicides alachlor and metolachlor. The solvent was removed by allowing it to evaporate at room atmosphere. Perez-Martinez et al. (Pest Manag Sci 2001, 57:688-694) disclose the same method for preparation of controlled release microcapsules of the pesticide norfluazon.

There remains an unmet need for nanoparticle formulations of water-insoluble pesticides compounds which can be produced by simple and cost-effective techniques.

SUMMARY OF THE INVENTION

The present invention provides redispersible powders and aqueous dispersions comprising nanoparticles of water-insoluble organic pesticide and other agrochemicals, and methods for their production. The invention is based, in part, on the unexpected discovery that a redispersible powder formulation or an aqueous dispersion, comprising high weight percentages of a water-insoluble pesticide in the form of nanoparticles, can be prepared from an oil-in-water microemulsion or nanoemulsion containing a water insoluble, non halogenated volatile organic solvent, from which organic solvent and/or water has been removed. The simultaneous removal of the water and the organic solvents, for example by spray drying, leads to immediate conversion of the dissolved organic pesticide, into solid nanoparticles. These nanoparticles exhibit surprising properties in view of their dissolution properties, degree of non-crystallinity and biological activity. The invention can be applied to nanoparticles of any water insoluble agrochemicals and pesticides, e.g., lambda-cyhalothrin and novaluron (Rimon®). The present invention also provides compositions comprising the nanoparticles of water-insoluble organic pesticides, and methods of use thereof to combat pests by application to crop or plants.

The process of the invention involves initially forming an oil-in-water emulsion, which can be a microemulsion or a nanoemulsion, and removing the solvent. The oil-in-water emulsion is formed by dissolving the poorly water soluble organic compound in an organic solvent with or without a hydrophobic polymer as the particle structure builder, and adding an aqueous solvent. In one embodiment, high-pressure homogenization or other high shear technique is used, resulting in a nanoemulsion having a droplet size of about 300 nm or less. In another embodiment, however, a thermodynamically stable microemulsion having a droplet size of about 30 nm or less is spontaneously formed without the use of high-pressure homogenization or high shear techniques. Regardless of the type of emulsion formed, this is followed by a solvent evaporation process resulting in aqueous dispersion, or in a lyophilized powder which is redispersible in an aqueous medium. By way of illustration and not by limitation, nanoparticles of the water-insoluble organic pesticide formed from the nanoemulsion typically have a particle size of 300 nm or less, and nanoparticles of the water-insoluble organic pesticide formed from the microemulsion have a particle size of about 30 nm or less.

Advantageously, the redispersable powder provides a product having a long shelf life, with enhanced dissolution properties, which if desired, can be converted to an aqueous dispersion, for example, immediately prior to use. Optimal solubility of a pesticide is often critical for its effective application and distribution in crops. Further, it is contemplated that formulating pesticides into nanoparticles may include the benefit of reducing exposure at process and at field application.

The nanoparticle formulations of the invention advantageously comprise a high percentage by weight of the water-insoluble organic pesticide in particulate form.

In a first aspect, the present invention provides a redispersible powder comprising nanoparticles of a water-insoluble organic pesticide, wherein the nanoparticles are in a particulate form. As used herein, the term “particulate form” means individual non-aggregated particles, excluding, e.g., nanoparticles dispersed in a matrix such as a polymeric bead.

Additional constituents of the redispersible powder such as polymers, (preferably non-cross linked polymers) and redispersion aids are present in the powder as separate entities and not as a part of the particles of the water-insoluble organic pesticide. Without wishing to be limited by any particular mechanism or theory, it is believed that the role of the polymers is to improve stability of the nanoparticles, to enable control of the dissolution rate, to prevent crystallization, and in addition, in the case of water soluble polymer, to aid the re-dispersion process. Suitable polymers include, but are not limited to, water insoluble polymers such as polylactic acid, cellulose acetate, methyl cellulose, ethyl cellulose, hydroxylpropyl methyl cellulose, poly(lactic-co-glycolic acid), hydroxylpropyl cellulose phthalate, and mixtures thereof. Alternatively, the polymer can be a water soluble polymer such as polyvinyl pyrrolidone (PVP), polyvinyl alcohol, carboxy methyl cellulose, hydroxy ethyl cellulose, polyethylene glycol, and mixtures thereof. Alternatively, the polymer can be a non-crosslinked polymer. Examples of a re-dispersion aid include, but are not limited to, a wetting agent, a disintegrant, a water soluble polymer, colloidal silica particles, sugars, mannitol and mixtures thereof. A currently preferred polymer is ethyl cellulose.

In one embodiment, the nanoparticles comprise at least about 50% by weight of the water-insoluble organic pesticide. In other embodiments, the nanoparticles comprise at least about 80% by weight, more preferably 85%, still more preferably 90% yet still more preferably 95% by weight of the water-insoluble organic pesticide. In another embodiment, the nanoparticles consist essentially of the water-insoluble organic pesticide. In another embodiment, the nanoparticles comprise at least about 5-80% of the redispersible powder, or if high pressure homogenization is used, the nanoparticles can typically comprise from about 5% to about 95% or more of the redispersible powder. Advantageously, preparation of the water-insoluble organic pesticide in nanoparticulate form significantly increases its solubility and rate of dissolution as compared to the same pesticide in unprocessed form, i.e., in a form which has not undergone any particle size reduction or other treatment to increase its solubility and rate of dissolution. Thus, in another embodiment, the solubility of the water-insoluble organic pesticide is at least about 5 times greater than the solubility of the water-insoluble organic pesticide in unprocessed form i.e. not in the form of the nanoparticles prepared by the invention. In another embodiment, the solubility of the water-insoluble organic pesticide is at least about 10 times greater than the solubility of the water-insoluble organic pesticide in unprocessed form. In another embodiment, the dissolution rate of the nanoparticles is at least about 5 times greater than the dissolution rate of the water-insoluble organic pesticide in unprocessed form. In yet another embodiment, the dissolution rate of the nanoparticles is at least about 10 times greater than the dissolution rate of the water-insoluble organic pesticide in unprocessed form.

In one embodiment, the nanoparticles have a diameter of about 300 nm or less, for example about 200 nm or less. Such nanoparticles are typically formed from nanoemulsions, which are in turn formed by mixing an organic phase containing the water-insoluble organic pesticide and optionally a polymer with an aqueous medium, using high pressure homogenization or high shear techniques (e.g., ultra-sonication). In another embodiment, however, the nanoparticles have a diameter of about 30 nm or less, for example about 5 to about 30 nm. Such nanoparticles are typically formed from thermodynamically stable microemulsions, which are in turn spontaneously formed by mixing an organic phase containing the water-insoluble organic pesticide with an aqueous medium without the use of high pressure homogenization or high shear techniques In one embodiment, the water-insoluble organic pesticide is selected from an insecticide, a herbicide, a fungicide, an acaricide, an algicide, an antimicrobial agent, biopesticide, a biocide, a disinfectant, a fumigant, an insect growth regulator, a plant growth regulator, a miticide, a microbial pesticide, a molluscide, a nematicide, an ovicide, a pheromone, a repellent, a rodenticide, a defoliant, a dessicant and mixtures thereof. One currently preferred pesticide is novaluron (Rimon®). Another currently preferred pesticide is lambda cyhalothrin.

In another embodiment, the insecticide is selected from the group consisting of benzoyl ureas such as novaluron, lufenuron, chlorfluazuron, flufenoxuron, hexaflumuron, noviflumuron, teflubenzuron, triflumuron and diflubenzuron; carbamates; pyrethroids such as cyhalothrin and isomers and isomer mixtures thereof, lambda-cyhalothrin, deltamethrin, tau-fluvalinate, cyfluthrin, beta-cyfluthrin, tefluthrin, and, bifenthrin; organophosphates such as azinfos-methyl, chlorpyrifos, diazinon, endosulfan, methidathion; neonicotinoids, and phenylpyrazoles such as imidacloprid, acetamiprid, thiacloprid, dinotefuran, thiamethoxam and fipronil.

In another embodiment, the fungicidally active compound is selected from the group consisting of conazoles such as epoxiconazole, hexaconazole, propiconazole, prochloraz, imazalil, triadimenol, difenoconazole, myclobutanil, prothioconazole, triticonazole and tebuconazole; morpholines such as dimethomorph, fenpropidine and fenpropimorph; strobilurins such as azoxystrobin, kresoxim-methyl and analogues; phthalonitriles such as chlorothalonil; and mancozeb; fluazinam; and pyrimidines such as bupirimate.

In another embodiment, the herbicide is selected from the group consisting of aryloxyphenoxy derivatives, aryl ureas, aryl carboxylic acids, aryloxy alkanoic acid derivatives such as clodinafop-propargyl and analogues thereof, fenoxaprop-p-ethyl and analogues thereof, propaquizafop, quizalafop and analogues thereof, dintroanilines such as pendimethalin and trifluralin; diphenyl ethers such as oxyfluorfen, imidazolinones, sulfonylureas such as chlorsulfuron, nicosulfuron, rimsulfuron, tribenuron-methyl, sulfonamides, triazines, and triazinones such as metamitron.

In another embodiment, the water-insoluble organic pesticide is in an amorphous form or a partially amorphous form. In another embodiment, an aqueous dispersion comprises the redispersible powder of the invention, and an aqueous medium.

In another embodiment, a pesticide composition comprises the redispersible powder of the invention, and at least one adjuvant. In another embodiment of the pesticide composition, the powder is packed within a capsule or a tablet or a granule. In another embodiment, the pesticide composition is in the form of an aqueous dispersion, and comprises the redispersible powder of the invention dispersed in an aqueous medium. In one embodiment, the nanoparticles constitute at least about 0.5% of the aqueous dispersion. In another embodiment, the nanoparticles constitute at least about 5.0% of the aqueous dispersion.

In another aspect, the present invention provides a process for preparing a redispersible powder comprising nanoparticles of a water-insoluble organic pesticide, the process comprising the steps of: (i) preparing an oil-in-water emulsion comprising a water-insoluble organic pesticide, a volatile water-immiscible organic solvent, water, and at least one surfactant; and (ii) removing the volatile water-immiscible organic solvent and the water so as to form the redispersible powder comprising the nanoparticles, wherein the nanoparticles are in a particulate form.

In one embodiment, the step of preparing the oil-in-water emulsion comprises: (i) dissolving the water-insoluble organic pesticide in the volatile water-immiscible organic solvent so as to form an organic phase; and (ii) mixing the organic phase with water and a surfactant so as to form the oil-in-water emulsion. In one currently preferred embodiment, the step of preparing the nanoemulsion includes the use of a high pressure homogenizer or a high sheer instrument, resulting in a nanoemulsion having a droplet size of less than about 300 nm. Nanoparticles obtained from said nanoemulsion typically have a diameter of less than about 300 nm. In another embodiment, however, the microemulsion is spontaneously formed, resulting in a thermodynamically stable microemulsion having a droplet size of less than about 30 nm. Nanoparticles obtained from said microemulsion typically have a diameter of less than about 30 nm.

In another embodiment, the volatile water-immiscible organic solvent and water are removed by spray drying or lyophilization. In another embodiment, the redispersible powder is further re-dispersed in water to form an aqueous dispersion of the nanoparticles.

In another embodiment, the water-immiscible organic solvent is selected from the group consisting of n-butyl acetate, sec-butyl acetate, isobutyl acetate, propyl acetate, toluene, xylenes, R(+)-limonene, hexane, pentane, heptane and mixtures thereof. In another embodiment, the water-insoluble organic pesticide is present in an amount of about 0.1 to about 20% by weight, the water-immiscible organic solvent is present in an amount of about 0.5 to about 50% by weight, the co-solvent is present from 0 to about 30% and the water is present in an amount of from about 20 to about 85% by weight, based on the total weight of the microemulsion. In another embodiment, the volatile water-immiscible organic solvent and the water are removed simultaneously In another embodiment, the microemulsion further comprises at least one polymer. Without wishing to be bound by any particular mechanism or theory, it is contemplated that the polymer functions in the particles as a matrix holding the active agent in the particle form. In one embodiment, the polymer is a water insoluble polymer selected from polylactic acid, cellulose acetate, methyl cellulose, ethyl cellulose, hydroxypropyl methyl cellulose, poly(lactic-co-glycolic acid), hydroxypropyl cellulose phthalate, and mixtures thereof. In another embodiment, the polymer is a water soluble polymer selected from the group consisting of poly-vinyl pyrrolidone (PVP), polyvinyl alcohol, carboxy methyl cellulose, hydroxy ethyl cellulose, polyethylene glycol, gum arabic and mixtures thereof. In another embodiment, the polymer is a non-crosslinked polymer. In another embodiment, the polymer is present in an amount of about 0.01 to about 10% by weight based on the total weight of the microemulsion. A currently preferred polymer is ethyl cellulose.

In another embodiment, the microemulsion further comprises a re-dispersion aid, Examples of a re-dispersion aid include, but are not limited to, a wetting agent, a disintegrant, a water soluble polymer, colloidal silica particles, sugars, mannitol and mixtures thereof.

In another embodiment, the microemulsion further comprises a co-solvent. Examples of a co-solvent include, but are not limited to, ethanol, 1-propanol, 2-propanol, n-pentanol, n-butanol, ethyl acetate, tetrahydrofuran, propylene glycol, formamide, glycerol, polyethylene glycol and mixtures thereof. In another embodiment, the co-solvent is present in an amount of about 5 to about 30% by weight based on the total weight of the microemulsion.

The dispersion is stabilized by a surfactant or a mixture of surfactants, exhibiting a unique ability to prevent formation of crystals, and aggregates, preventing some of the well-known instability mechanisms. In one embodiment, the surfactant is selected from the group consisting of a cationic surfactant, an anionic surfactant, an amphoteric surfactant, a nonionic surfactant and mixtures thereof. In specific embodiments, the anionic surfactant is selected from the group consisting of an alkyl benzene sulfonate (e.g., sodium alkyl naphthalene sulfonate), sodium dodecyl sulfate, sodium sulfosuccinate, sodium lauryl sulfate, alkyl naphthalene sulfonate condensate sodium salt, sodium stearate, and mixtures thereof; the nonionic surfactant is selected from the group consisting of an ethoxylated sorbitan ester, a sorbitan ester, an organosilicone surfactant, a polyglycerol ester, a sucrose ester, a poloxamer, an alkyl polyglucoside, polyalkyleneoxide modified heptamethyltrisiloxanes, and allyloxypolyethylene glycol methylether and mixtures thereof; the amphoteric surfactant is lecithin; and the cationic surfactant is selected from the group consisting of cetyl trimethyl ammonium bromide, cetyl trimethyl ammonium chloride, and mixtures thereof. In another embodiment, the surfactant is present in an amount of about 5 to about 35% by weight based on the total weight of the microemulsion. A currently preferred surfactant is Morwet® (sodium n-butyl naphthalene sulfonate). Another currently preferred surfactant is Silwet® L-77 (an organosilicone surfactant comprising a blend of polyalkyleneoxide modified heptamethyltrisiloxane and allyloxypolyethylene glycol methyl ether.

In another embodiment, the water-insoluble organic pesticide is in an amorphous form or a partially amorphous form. In another embodiment, the process further comprises the step of crystallizing the nanoparticles, thereby providing crystalline organic nanoparticles. In another embodiment, the nanoparticles are crystallized by aging. Another embodiment provides a redispersible powder comprising nanoparticles of a water-insoluble organic pesticide, prepared by the process described herein. Another embodiment provides an aqueous dispersion, comprising nanoparticles of a water-insoluble organic pesticide, prepared by the process described herein.

In another aspect, the present invention provides a process for preparing an aqueous dispersion comprising nanoparticles of a water-insoluble organic pesticide, the process comprising the steps of: i) preparing an oil-in-water emulsion comprising a water-insoluble organic pesticide, a polymer, a volatile water-immiscible organic solvent, water, and at least one surfactant; and (ii) removing the volatile water-immiscible organic solvent so as to form an aqueous dispersion comprising the nanoparticles, wherein the nanoparticles are in a particulate form.

In one particular embodiment, the process of the invention comprises the steps of:
  (1) dissolving a poorly water-soluble active agent in an organic volatile solvent;
  (2) providing an oil-in-water emulsion comprised of the organic phase and an aqueous phase;
  (3) providing energy to the emulsion to form a submicron droplets or fine dispersion, preferably using high shear methods such as high pressure homogenization or microfluidizer, so as to obtain a nanoemulsion; and
  (4) removing the volatile organic solvent by means of vacuum evaporation to obtain a fine dispersion of agro-chemically active nanoparticles;

In one particular embodiment, the process of the invention comprises the steps of:
  (1) dissolving a poorly-water-soluble active agent in an organic volatile solvent;

(2) providing a spontaneously formed, thermodynamically stable, oil-in-water microemulsion comprised of the organic phase and an aqueous phase; and (3) removing the volatile organic solvent by means of vacuum evaporation to obtain a fine dispersion of agrochemically active nanoparticles;

In one particular embodiment, there is a possibility to lyophilize or spray dry the aqueous dispersion into a powder. Prior to application, the powder is redispersed in water, where only mild agitation is needed. Some fine particles will appear, regaining their nanometric size.

Another embodiment provides an aqueous dispersion, comprising nanoparticles of a water-insoluble organic pesticide, prepared by the process described herein. Depending on which type of compounds are used to sustain a non-homogenous dispersion in a stable form (i.e., to prevent the oily droplets from coalescing and aggregating together, which is highly undesirable), these dispersions can be in the forms of emulsions, colloids, liposomes, micelles, and the like.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1: shows light scattering analysis of lambda-cyhalothrin particles.

DETAILED DESCRIPTION OF THE INVENTION

The present invention relates to the preparation of pesticide and other agrochemical nanoparticles. The methods of the present invention are useful for the preparation of an aqueous dispersion of water-insoluble pesticides or a redispersible powder capable or redispersing nanoparticles in water. The aqueous dispersion contains the water insoluble pesticide, and additives such as polymers, surfactants and wetting agents in order to maintain its size, structure and biological activity. Upon redispersing the powder, it will disperse into nanoparticles of the agrochemical by mild manual shaking without the need of applying mechanical energy. Accordingly, at the appropriate powder to water ratio, the particles composing the powder will regain their original size and concentration.

There are an ever-increasing number of active agents being formulated that are insoluble in aqueous solutions. Most of them are pharmaceutically active, to be delivered at a very low concentrations for in vivo delivery. Agrochemicals are another family of active agents encountered with similar problems during formulating them into accessible product to apply: Most are water insoluble, forcing the use of non-environmentally solvents in order to apply them. Similar efforts to those made to prepare water-immiscible drugs for in vivo delivery are applied in order to deliver the agrochemical into the plant. These usually involve dissolving the active agents in non-environmentally and unhealthy solvents. Further, some of the current methods present a potential safety risk, exposing the operator to irritant to toxic levels of the pesticides, while some having long term side effects like neural effects. Formulating agrochemicals into nanoparticles may include the benefit of reducing exposure at process and at field application. Another important difference is that, unlike pharmaceutical agents used in very low concentrations, agrochemicals require relatively high concentrations needed to control pest.

In one embodiment, the process of the invention is based the following steps: the first step is formation of an emulsion (o/w—oil in water), where the organic phase contains the pesticide and a polymer. Such emulsion is, in one embodiment, a nanoemulsion having droplets of about 300 nm or less, prepared using high-pressure homogenization or other high shear methods (e.g., ultrasonication). In another embodiment, the emulsion is a microemulsion having droplets of about 30 nm or less, which microemulsion is thermodynamically stable, and is formed without using any high pressure homogenization or high shear techniques. The removal of the solvent by solvent evaporation (HP/SE), forms an aqueous dispersion (solvent-free) of nanoparticles containing the active agent, preferably agrochemical. By lyophilization or spray-drying, using additives such as wetting agents, a fluffy powder is obtained. The present invention overcomes several significant problems in the prior art:

1. The present invention utilizes environmentally friendly solvents to replace the current chlorinated solvents used widely in "high pressure/solvent evaporation" method. For example, in order to dissolve novaluron, it was found that isobutyl acetate, which is appropriate for our method, i.e., low water solubility and high volatility, is able to dissolve both the agrochemical and the polymer ethyl cellulose.

2. The methods of the invention allow for loading of extremely high concentrations—up to 5% wt of the active agent in the dispersion, or even 45% in the powder form. By way of comparison some prior art processes regarding pharmaceuticals refer to less then 0.1% wt active agent. According to the present invention, an aqueous dispersion of lambda-cyhalothrin was established at a concentration of 5% wt.

3. Prior art dispersions exhibit are inherently unstable. These tend to form aggregates, coalescence, and crystallize. In contrast, the dispersions of the present invention are stable, i.e., they maintain nano-sized particles for weeks.

4. The polymer used in a preferred embodiment—ethyl cellulose is an environmentally—friendly polymer. Another advantage of this polymer is that it is less expensive than fatty polyesters used previously. In addition, it was found that ethyl cellulose also contributed to the stabilization mechanism.

5. The present invention results in the formation of a re-dispersible powder, which easily re-disperses into nanoparticles upon the addition of water, using no mechanical means. This is a tremendous advantage to the user, e.g., a farmer, who has no mean of applying sophisticated means of agitation. The present invention is based on the discovery of how to select the right materials and amounts in order to establish stable powder with up to 45% wt of the active agent. For example, lyophilizing the obtained dispersion just after the evaporation yields crude flakes unable to re-disperse when introduced to water. Again, a careful selection of wetting agents was made, all acceptable in agricultural formulations, in order to regain the nano dimensions of the particle. For example, Morewet® was added to the aqueous dispersion with particles in the size of 180 nm, (prior to lyophilization). The resulting powder exhibited 300 nm particles as were measured with malven zetasizer.

The invention thus relates, in one embodiment, to a dry redispersible powder comprising nanoparticles of a water-insoluble organic pesticide, wherein the nanoparticles are in a particulate form. A redispersible powder provides a product having a long shelf life and possessing minimal bulk and weight properties (as compared to a liquid form). The nanoparticles have a better dissolution rate and better solubility then the conventional microparticles, and this may lead to enhanced applicability and bioavailability, for example, for poorly soluble insecticides and herbicides. As required, a redispersible powder can be converted to an aqueous dispersion upon contact with an aqueous medium such as water in order to provide a spray formulation of a pesticide. In another embodiment, the present invention relates to an aqueous dispersion comprising nanoparticles of a water-insoluble organic pesticide, wherein the nanoparticles are in a particulate form. Such redispersible powders and aqueous dispersions can be used for a variety of poorly water soluble pesticides, including, for example, insecticides, herbicides, fungicides, acaricides, growth regulators, rodenticides, defoliants, repellents and chemosterilants. Use of the formulations can positively impact on a variety of pesticide characteristics relating to chemical stability, safety, incompatibility, solubility, suspension, foaming, drift, evaporation, volatilization, phytotoxicity, surface tension, droplet size and coverage. The invention further relates to processes for preparing such redispersible powders and aqueous dispersions, wherein the processes comprise preparation of an oil-in-water emulsion (microemulsion or nanoemulsion) and subsequent solvent removal.

Definitions

The term "nanoparticles" as used herein describes particles having an average diameter of between about 1 nanometer (nm) and about 1000 mm. Nanoparticles of a particular molecular entity or compound exhibit physico-chemical properties that are significantly different from that of larger forms of the same molecular entity or compound. Preferably, the nanoparticles of the present invention have a diameter of less than about 100 nm, more preferably less than 50 mm, and even more preferably less than about 30 nm.

Solubility is defined as the concentration of the solute in a saturated solution. The solubility of compounds varies in accordance with factors such as temperature, the type of solvent, the pH of the solution, and atmospheric pressure. Further, decreased size leads to increased solubility and dissolution rate. As described in a review by Sasson et al. (in *Insecticide Design Using Advanced Technologies*, edited by: Isaac Ishaaya, Ralf Nauen and Rami Horowitz, Springer-Verlag, Heidelberg, Germany), size reduction of a drug particle, particularly to the submicron level, leads to simultaneous enhancement of both the saturation solubility $C_s$ and the dissolution rate dC/dt. The saturation solubility increases with decreasing particle size according to the Ostwald-Freundlich Equation, also known as the Gibbs-Thomson Equation and as the Kelvin Equation (Equation 1):

$$\frac{S(d)}{S_0} = \exp\frac{\gamma V_m}{RTd} \qquad \text{Equation 1}$$

where S(d) is the solubility (mol/kg H$_2$O) of crystals with inscribed diameter d (m) at temperature T (° K.); $V_m$ is the molar volume (m$^3$/mol), $\gamma$ is the surface free energy (surface tension) (mJ/m$^{2-}$); R is the gas constant (8314.5 mJ/mol.° K.); and $S_0$ is the solubility of the bulk material (d→∞). With all other factors kept constant the solubility increases with smaller particle size. However for the solubility S(d) to differ significantly from the solubility $S_0$ of the bulk material (i.e. the ratio S(d)/$S_0$>>1) the exponential term needs to be much smaller than one. This occurs only with particle size in the nanometric range.

In addition, the dissolution rate (dC/dt) is directly proportional to the surface area and to the concentration gradient. This is determined by the Noyes-Whitney Equation (Equation 2):

$$\frac{dC}{dt} = \frac{DA(C_S - C_B)}{h} \qquad \text{Equation 2}$$

where C is concentration (mole/liter), D is the diffusion coefficient of the drug, h is the effective diffusion boundary layer, A is the effective surface area, $C_S$ is the saturation solubility of the drug (equivalent to S in Equation 1) and $C_B$ is the bulk concentration of the drug. Since upon decrease of the particles into the nanometric range, both $C_s$ and A increase, the effect on the dissolution rate is significant.

The solubility of compounds is expressed as the number of milliliters of solvent in which one gram of solute can dissolve. Where the exact solubility of various compounds cannot be precisely determined general quality terms are used to describe the solubility of a specific compound, typically with reference to other compounds. Solubility may also be expressed in terms of molarity, percentage, and molality. Typically, compounds defined as water insoluble are those that require more than 1 ml part of solvent per 10 mg of solute (1% w/v).

The term "in a particulate form" as used herein denotes discrete, individual, non-aggregated particle entities composed of a water-insoluble organic pesticide, such that the water-insoluble organic pesticide is not enclosed within, incorporated within, embedded within, contained within or associated with any encapsulation form, bead, carrier, matrix or similar delivery agent.

The term "dissolution factor" as used herein describes the relative dissolution rate of a solute in a solvent. In particular, the term describes the relative time required to dissolve specific proportions of a solvent and a solute which are required in order to effect dissolution of the solute in the solvent. In addition it describes the increase in maximal solubility compared to the maximal solubility of the bulk material.

The term "emulsion" as used herein includes both microemulsions and nanoemulsions, each of which are further defined herein.

The term "microemulsion" as used herein includes both oil-in-water microemulsions and "reverse" microemulsions which are water-in-oil microemulsions. An oil-in-water microemulsion is a translucent to transparent dispersion of an organic phase in an aqueous phase, having a droplet diameter size in the nanometer range (1-50 nm). It is thermodynamically stable and is generally spontaneously self emulsifying upon mixture of appropriate surfactant(s), cosurfactant(s), solvent(s), cosolvent(s), water insoluble material and water (see for example, Friberg et al. (1987) *Microemulsions Structure and Dynamics*, CRC Press Inc., Boca Raton, Fla.). In contrast, oil-in-water emulsions having droplets of larger diameter can be thermodynamically unstable and/or require high shear forces to induce their formation. A "reverse microemulsion" is a water-in-oil microemulsion which is a translucent to transparent dispersion of an aqueous phase in an organic phase and it is also thermodynamically stable.

The term "nanoemulsion" as used herein includes both oil-in-water nanoemulsions and "reverse" nanoemulsions which are water-in-oil nanoemulsions. An oil-in-water nanoemulsion typically has a droplet diameter size of 300 nm or less. It is typically formed using high pressure homogenization or high shear techniques, e.g., ultra-sonication.

The term "pesticide" as used herein refers to a chemical used for plant, crop or livestock protection against unwanted organisms ("pests"). A water-insoluble organic pesticide refers to an organic pesticide which is insoluble or poorly soluble in water. Pesticides include insecticides, herbicides, fungicides, acaricides, algicides, antimicrobial agents, biopesticides, biocides, disinfectants, fumigants, insect growth regulators, plant growth regulators, miticides, microbial pesticides, molluscides, nematicides, ovicides, pheromones, repellents, rodenticides, defoliants, dessicants and mixtures thereof. Pests include invertebrates such as insects, mites, slugs, snails, nematodes, flatworms, millipedes, pathogenic protozoa, weeds, fungi, moulds, bryophites, lichens, algae, yeasts, bacteria and viruses, as well as vertebrates such as rodents, rabbits and pigeons. Pesticides further include, but are not limited to organophosphate pesticides, carbamate pesticides, organochlorine insecticides and pyrethroid pesticides. Other examples of pesticides are disclosed in sources such as *Recognition and Management of Pesticide Poisonings* (US Environmental Protection Agency), the contents of which are incorporated by reference herein.

Insecticides kill insects and other arthropods. Herbicides kill weeds and other vegetation that grow in unwanted locations. Fungicides kill fungi, including blights, mildews, molds, and rusts. Acarcides (also called miticides) kill mites in plants. Algicides control algae in lakes, canals; swimming pools, water tanks, and other sites. Antimicrobial agents kill microorganisms including bacteria viruses, parasites and protozoa. Biopesticides are specific types of pesticides derived from such natural materials as plants, bacteria, and certain minerals. Biocides kill microorganisms. Disinfectants kill or inactivate disease-producing microorganisms on inanimate objects. Fumigants produce gas or vapor intended to destroy pests in buildings or soil. Insect growth regulators disrupt the molting, maturity from pupal stage to adult, or other life processes of insects. Plant growth regulators are substances (excluding fertilizers or other plant nutrients) that alter the expected growth, flowering, or reproduction rate of plants. Microbial pesticides are microorganisms that kill, inhibit, or out compete pests, including insects or other microorganisms. Molluscicides kill snails and slugs. Nematicides kill nematodes (microscopic, worm-like organisms that feed on plant roots). Ovicides kill eggs of insects and mites. Pheromones are biochemicals used to disrupt the mating behavior of insects. Repellants repel pests, including insects (such as mosquitoes) and birds. rodenticides control mice and other rodents. Defoliants cause leaves or other foliage to drop from a plant, usually to facilitate harvest. Dessicants promote drying of living tissues, such as unwanted plant tops. Biopesticides include: (1) microbial pesticides; (2) Plant-Incorporated-Protectants (PIPs), and (3) biochemical pesticides. Microbial pesticides can control many different kinds of pests, although each separate active ingredient is relatively specific for its target pest[s]. For example, there are fungi that control certain weeds, and other fungi that kill specific insects. The most widely used microbial pesticides are subspecies and strains of *Bacillus thuringiensis*, or Bt. Each strain of this bacterium produces a different mix of proteins, and specifically kills one or a few related species of insect larvae. While some Bt's control moth larvae found on plants, other Bt's are specific for larvae of flies and mosquitoes. The target insect species are determined by whether the particular Bt produces a protein that can bind to a larval gut receptor, thereby causing the insect larvae to starve. PIPs are pesticidal substances that plants produce from genetic material that has been added to the plant. For example, plants transformed with the gene encoding the Bt pesticidal protein. Biochemical pesticides are naturally occurring substances that control pests by non-toxic mechanisms, for example, insect sex pheromones, that interfere with mating, as well as various scented plant extracts that attract insect pests to traps.

In another embodiment, the insecticide is selected from the group consisting of benzoyl ureas such as novaluron, lufenuron, chlorfluazuron, flufenoxuron, hexaflumuron, noviflumuron, teflubenzuron, triflumuron and diflubenzuron; carbamates; pyrethroids such as cyhalothrin and isomers and isomer mixtures thereof, lambda-cyhalothrin, deltamethrin, tau-fluvalinate, cyfluthrin, beta-cyfluthrin, tefluthrin, and, bifenthrin; organophosphates such as azinfos-methyl, chlorpyrifos, diazinon, endosulfan, methidathion; neonicotinoids, and phenylpyrazoles such as imidacloprid, acetamiprid, thiacloprid, dinotefuran, thiamethoxam and fipronil;

In another embodiment, the fungicidally active compound is selected from the group consisting of conazoles such as epoxiconazole, hexaconazole, propiconazole, prochloraz, imazalil, triadimenol, difenoconazole, myclobutanil, prothioconazole, triticonazole and tebuconazole; morpholines such as dimethomorph, fenpropidine and fenpropimorph; strobilurins such as azoxystrobin, kresoxim-methyl and analogues; phthalonitriles such as chlorothalonil; and mancozeb; fluazinam; and pyrimidines such as bupirimate.

In another embodiment, the herbicide is selected from the group consisting of aryloxyphenoxy derivatives, aryl ureas, aryl carboxylic acids, aryloxy alkanoic acid derivatives such as clodinafop-propargyl and analogues thereof, fenoxaprop-p-ethyl and analogues thereof, propaquizafop, quizalafop and analogues thereof, dintroanilines such as pendimethalin and trifluralin; diphenyl ethers such as oxyfluorfen, imidazolinones, sulfonylureas such as chlorsulfuron, nicosulfuron, rimsulfuron, tribenuron-methyl, sulfonamides, triazines, and triazinones such as metamitron.

A currently preferred insecticide is lambda cyhalothrin. Another currently preferred insecticide is novaluron (Rimon®).

The oil-in-water emulsion of the present invention is a dispersion or emulsion of droplets of a water-insoluble, volatile organic solvent in an aqueous medium, with the droplets having a solvent core surrounded by an interfacial film of at least one surfactant. The surfactant(s) function in emulsifying the water-insoluble organic pesticide, wherein the emulsification process denotes the formation of the droplets dispersed within the aqueous phase. The droplets contain dissolved organic, water insoluble pesticide, defined as the "active material".

In one embodiment, the present invention provides a method for preparing a redispersible powder of a water-insoluble organic pesticide by preparing an oil-in-water emulsion, followed by removing the liquid components i.e. the volatile water immiscible organic solvent and the water so as to form the redispersible powder. The water-insoluble organic compound and the water are preferably removed simultaneously, but can also be removed sequentially, in any order. The microemulsion used in this method comprises a water-insoluble organic pesticide, a volatile water immiscible organic solvent, water and at least one surfactant. The microemulsion can further comprise additional components, in particular, at least one polymer, a re-dispersion aid or a co-solvent. Advantageously, the redispersible powder can be further dispersed in an aqueous medium e.g., water, to produce an aqueous dispersion.

In another embodiment, the present invention provides a method for preparing an aqueous dispersion of a water-insoluble organic pesticide by, preparing an oil-in-water microemulsion or nanoemulsion, followed by removing the volatile water immiscible organic solvent so as to form the aqueous dispersion. A polymer is preferably added to the microemulsion or nanoemulsion. Thus, in accordance with this embodiment, the microemulsion comprises a water-insoluble organic pesticide, a volatile water-immiscible organic solvent, a polymer, water, and at least one surfactant. The second step of this method involves removal of the volatile water-immiscible organic solvent but not the water, so that an aqueous medium remains. The microemulsion or nanoemulsion can further comprise a co-solvent.

An adjuvant is a substance which enhances or modifies the chemical and/or physical characteristics of a pesticide, but has no pesticidal activity of its own. Depending on their type, adjuvants can enhance wetting, spreading, sticking, emulsifying, dispersing and biological activity. Adjuvants include wetting agents, crop oil concentrates, spreaders, stickers, buffering agents, foaming and anti-foaming agents, dispersing agents and drift control agents.

According to the invention described herein, the volatile water immiscible organic solvent is one which is effective for dissolution of the water-insoluble organic pesticide, and preferably is one which is environmentally friendly. The prior art typically uses halogenated solvents having, exceptional dissolution ability and a suitable volatility requested on removal. However, these solvents, such as dichloromethane and chloroform are phasing out of industrial usage due to restricting regulation. In order to maintain the dissolution ability, less environmentally toxic solvents are proposed—such as aromatics and acetates. Further, the volatile water immiscible organic solvent is preferably volatile at the concentration used, such that it can be removed from the oil-in-water emulsion in the second step of the processes described herein. The volatile water immiscible organic solvent for a pesticide, is one which is environmentally acceptable in trace amounts Appropriate volatile water immiscible organic solvents include for example, n-butyl acetate, sec-butyl acetate, isobutyl acetate, propyl acetate, amyl acetate toluene, xylenes, R(+)-limonene, hexane, pentane, heptane cyclohexane and mixtures thereof.

Alternatively, dissolution of the water-insoluble organic pesticide can be achieved using the volatile water immiscible organic solvent in combination with a co-solvent which is either miscible or immiscible with water. Suitable co-solvents include for example, ethanol, 1-propanol, 2-propanol, n-pentanol, n-butanol, ethyl acetate, tetrahydrofuran, propylene glycol, formamide, glycerol, polyethylene glycol and mixtures thereof.

According to the invention described herein, the surfactant is a surface-active agent which increases the emulsifying, foaming, dispersing, spreading and wetting properties of a product. The surfactant should acceptable for agrochemical formulations. Suitable surfactants include cationic surfactants, anionic surfactants, amphoteric surfactants, nonionic surfactants, and mixtures thereof. Cationic surfactants include for example, cetyl trimethyl ammonium bromide, cetyl trimethyl ammonium chloride, and mixtures thereof. Anionic surfactants include for example, alkyl benzene sulfonates, naphthalene sulfonates condensate sodium salts, sodium dodecyl sulfate, sodium sulfosuccinate, sodium stearate, and mixtures thereof. Amphoteric surfactants include various lecithins, such as egg lecithin, soya bean lecithin, synthetic saturated lecithins such as dimyristoyl phosphatidyl choline, dipalmitoyl phosphatidyl choline and distearoyl phosphatidyl choline, and synthetic unsaturated lecithins such as dioleyl phosphatidyl choline and dilinoleyl phosphatidyl choline. Nonionic surfactants include for example, ethoxylated sorbitan esters, sorbitan esters, polyglycerol esters, organosilicones, sucrose esters, poloxamers, alkyl polyglucosides, polyalkyleneoxide modified heptamethyltrisiloxanes, and allyloxypolyethylene glycol methylether and mixtures thereof. Another suitable surfactant is a phospholipid.

According to the invention described herein, the re-dispersion aid is an agent which promotes dispersion of the powder of nanoparticles of the water-insoluble organic pesticide within an aqueous phase. Suitable dispersion aids include for example, wetting agents, disintegrants, water soluble polymers, colloidal silica particles, sugars, mannitol and mixtures thereof. Some of the preferred additives of the present invention, e.g., mannitol, allow the fast penetration of water so that a fluffy powder is obtained. Another preferred additive is Aerosil® 200 aqueous dispersion (silica nanoparticles), which is suitable for settling between the nanoparticles of pesticides, preventing those from aggregating and regaining their original size. Another preferred additive is Morwet® D 425 which enhances the penetration of water and re-dispersion of the powder.

According to the invention described herein, a polymer is optionally included in the oil-in-water emulsion. The polymer can be a water insoluble polymer, including for example, polylactic acid, cellulose acetate, methyl cellulose, ethyl cellulose, hydroxylpropyl methyl cellulose, poly(lactic-co-glycolic acid), hydroxylpropyl cellulose phthalate, and mixtures thereof. The polymer can be a water soluble polymer, including for example, polyvinyl pyrrolidone (PVP), polyvinyl alcohol, carboxy methyl cellulose, hydroxy ethyl cellulose, polyethylene glycol, and mixtures thereof. The polymer is preferably a non-cross linked polymer. The polymer should further be environmentally acceptable. The present invention preferably utilizes ethyl cellulose, an environmentally friendly polymer (in terms of degraded products). The polymer functions as the particle structure builder affecting the particle structure.

To prepare the oil-in-water emulsions of the invention, an organic phase and an aqueous phase are separately prepared and then mixed together to form the emulsion. To prepare the organic phase, a water-insoluble organic pesticide is dissolved in a volatile water immiscible organic solvent, optionally in combination with a co-solvent. The aqueous phase is prepared by combination of the aqueous components, usually including the surfactant and water, and optionally in combination with a polymer and/or dispersion aid. Alternatively, the polymer, the re-dispersion aid and/or the surfactant can be mixed in the organic phase. The aforementioned dissolution steps can be spontaneous or can be carried out using various mechanical stirring instruments The temperature and length of time for carrying out the dissolution steps can be adjusted as required to achieve improved results. The respective solvent and aqueous phases so obtained are then mixed together to obtain a microemulsion. The temperature and length of time for carrying out the mixing of the phases can be adjusted as required to achieve improved results. In particular embodiments, the emulsion is a microemulsion formed spontaneously upon mixing of the phases by simple mechanical means such as vortexing. In a currently preferred embodiment, however, the emulsion is a nanoemulsion formed by high shear methods or by high-pressure homogenizer or a microfluidizer in pressures up to 30,000 psi, resulting in low dispersity index nanodrops containing the active agent. Several prior art references utilize high pressure gear to form sub micron drops. U.S. Pat. No. 6,706,863, the contents of which are incorporated by reference herein, uses high pressure homogenizer to emulsify montan wax in water, in order to yield nanodrops. Quickly after the 'grinding', the organic volatile phase is removed by rotary evaporation at heating and at a reduced pressure of ~10 mm Hg, resulting in an aqueous dispersion of particles.

According to specific embodiments of the methods of the invention for preparing a redispersible powder and for preparing an aqueous dispersion, the oil-in-water emulsion is prepared by a method which involves (i) dissolving the water-insoluble organic pesticide in the volatile water-immiscible organic solvent so as to form an organic phase; and (ii) mixing the organic phase with water and a surfactant so as to form the oil-in-water emulsion. In one embodiment, the preparation of the emulsion does not involve use of a high pressure homogenizer or a high shear instrument, so as to form a thermodynamically stable microemulsion. In another embodiment, the step of forming the emulsion further comprises the use of a high pressure homogenizer or a high sheer instrument, so as to form a nanoemulsion. This embodiment may facilitate industrial scale production of the formulations of the invention.

The percent weight proportions of the various components used in the preparation of the microemulsion or nanoemulsion can be varied as required to achieve optimal results. According to one embodiment, the water-insoluble organic pesticide is present in an amount of about 0.1 to about 20% by weight, the water-immiscible organic solvent is present in an amount of about 0.5 to about 50% by weight, the surfactant is present in an amount of about 5 to about 30% by weight and the water is present in an amount of from about 20 to about 85% by weight, based on the total weight of the microemulsion or nanoemulsion. When a polymer is used in the preparation of the microemulsion or nanoemulsion, according to one embodiment it is present in an amount of about 0.01 to about 10% by weight based on the total weight of the microemulsion or nanoemulsion. When a co-solvent is used in the preparation of the microemulsion or nanoemulsion, according to one embodiment it is present in an amount of about 2 to about 30% by weight based on the total weight of the microemulsion or nanoemulsion. Alternate percent weight proportions are also envisioned. For example, the water-insoluble organic pesticide can be present in an amount of up to about 30% by weight; the water-immiscible organic solvent can be present in an amount of up to about 70% by weight; the surfactant can be present in an amount of up to about 40% by weight and the water can be present in an amount of from about 10 to about 90% by weight, based on the total weight of the microemulsion or nanoemulsion. In the method of preparing a redispersible powder, the final step involves removing the volatile water immiscible organic solvent and the water, thus yielding the redispersible powder. In one embodiment, the solvent evaporation step is sufficient to remove all of the liquid components from the microemulsion or nanoemulsion, so that the powder has optimal handling characteristics e.g. is not "sticky", does not contain any potential breeding ground for contamination by microorganisms, and does not contain excessive amount of residual solvents. The removing step can be carried out by means known in the art, for example, lyophilization or spray drying.

For spray drying, the microemulsion or nanoemulsion can be directly filled into a laboratory spray dryer. Operating conditions can be varied according to the instrument and the experience of one skilled in the art. One set of operating conditions can include for example, air inlet temperature of 115-130° C., air outlet temperature of 65-75° C., feed rate of 28-30 mL/min and air flow rate of 450-550 m$^3$/h. All these parameters can be modified in order to meet the required properties of the resulting powder, which takes into consideration the physical behaviour of all the components under these conditions.

The solvent removal is an important step defining the initial (prior to lyophilization, in case the preparation is not through simultaneous removal of the organic solvents and the water) features of the particles such as size, crystallinity and morphology. There are many ways to remove the solvent, from the simplest way allowing the solvent to diffuse out at atmospheric pressure overnight, or using extraction that requires large amounts of solvents, but most refer to vacuum as the main step. U.S. Pat. No. 6,835,396, the contents of which are incorporated by reference herein, reports that rapid solvent evaporation may result in an amorphous particle solid state, while other claim for crystalline state of the active agent in the particle. The applicants of the present invention have discovered that the particles exhibit low crystalline content comparing to the pure technical agrochemical, as verified using differential scanning calorimetry (DSC) and X-ray diffraction (XRD) measurements. Optimal conditions, including for example time and temperature, for removing the organic volatile water-immiscible solvent and water can be determined empirically. The amount of organic solvent that remains after evaporation can be determined by HPLC.

The powder thus obtained upon removal of organic volatile water-immiscible solvent and water can be used as the final product, such as a powder of poorly soluble insecticide. It can also b re-dispersed in an aqueous medium, such as water, to yield an aqueous dispersion. The aqueous dispersion is usually obtained by gentle mixing, and is semi transparent and stable, such that there is no settling or precipitation.

In the method of preparing an aqueous dispersion, the final step involves removing the volatile water immiscible organic solvent, thus yielding the aqueous dispersion. In one embodiment, the solvent evaporation step is sufficient to remove the water immiscible organic solvent from the microemulsion or nanoemulsion, so that the aqueous dispersion does not contain excessive amount of residual solvents. In one embodiment of the method of preparing an aqueous dispersion, the solvent is removed under reduced pressure, such as, by rotovap equipment.

After solvent evaporation and redispersal of the redispersable powder, the presence of nanoparticles after redispersing the powder or in water can be ascertained microscopically after by using cryo-transmission electron microscopy (Cryo-TEM). Prior to microscopic observation, a sample of the redispersable powder redispersed in water or the aqueous dispersion can be purified to remove excess surfactant. For purification, the sample can be ultrafiltered through a polysulfone membrane (cut off 300,000), washed with de-ionized water and centrifuged.

Afterwards, the sample is prepared for the observation in a Controlled Environment Vitrification Chamber. A thin film of the sample is prepared and immersed into liquid ethane at −183° C. This procedure enables vitrification of the sample without any structural changes. The sample is kept at the temperature under −170° C. for approximately 30 minutes till the equilibrium is reached, and then it is observed, while kept at low temperature.

The diameter size of the nanoparticles present in the redispersable powder or in the aqueous dispersion can be ascertained by light scattering measurements, for example using a dynamic light scattering instrument, such as the Zetasizer Nano ZS (Malvern Instruments, UK). The particle size can be determined either by volume distribution or by number distribution. The methods described herein generally yield nanoparticles of diameter less than 500 nm. The nanoparticles can be of diameter in the range 400 to 500 nm, 300 to 400 nm, 200 to 300 nm, 100 to 200 nm, 50 to 100 nm, 10 to 50 nm or 1 to 5 nm. In specific embodiments of the methods and of the redispersible powder disclosed herein, the nanoparticles have a diameter of less than about 100 nm, preferably less than about 50 nm, more preferably less than about 30 nm, and more preferably in the range of about 5 to about 50 nm. Depending on which method was used to form the emulsion, nanoparticles having different diameters can be obtained.

The nanoparticles present in the redispersable powder or in the aqueous dispersion of the invention are in a particulate form. This means that the nanoparticles are discrete, individual, non-aggregated particle entities composed of a water-insoluble organic pesticide, such that the water-insoluble organic pesticide is not enclosed within, incorporated within, embedded within, contained within or associated with any encapsulation form, bead, carrier, matrix or similar delivery agent.

In specific embodiments of the methods of the invention and of the redispersible powder, the nanoparticles comprise at least about 50% by weight of the water-insoluble organic pesticide. In other embodiments, the nanoparticles comprise at least about 80% by weight of the water-insoluble organic pesticide. In other embodiments, the nanoparticles consist essentially of the water-insoluble organic pesticide. In a specific embodiment of the method for preparing a redispersable powder, the nanoparticles comprise at least about 5% of the redispersible powder. In a specific embodiment of the method for preparing an aqueous dispersion, the nanoparticles comprise at least about 0.5% of the aqueous dispersion. In another embodiment, the nanoparticles comprise at least about 5.0% of the aqueous dispersion.

In specific embodiments of the methods of the invention and of the redispersible powder, the active molecule is present at 0.05%-90% of the total weight of the powder.

The methods of the invention described herein provide nanoparticles of a water-insoluble organic pesticide, which have significantly increased solubility and dissolution rate as compared to the same compound in unprocessed form i.e., in a form which has not undergone any particle size reduction or other treatment to increase its solubility or dissolution rate. This is highly advantageous for the preparation of diverse pesticides, in which the active agents or other important components are usually insoluble or at best, poorly soluble. Thus, manufacturing and delivery solutions can be provided for example, for agricultural compositions e.g., poorly soluble pesticides. The invention provides a means of providing such compounds at relatively high concentrations, compared to unprocessed forms.

Thus, in one embodiment, the solubility of the water-insoluble organic pesticide is at least about 5 times greater than the solubility of the water-insoluble organic pesticide in unprocessed form i.e. not in the form of the nanoparticles prepared by the invention. In another embodiment, the solubility of the water-insoluble organic pesticide is at least about 5 times greater than the solubility of the water-insoluble organic pesticide in unprocessed form. In another embodiment, the dissolution rate of the nanoparticles is at least about 5 times greater than the dissolution rate of the water-insoluble organic pesticide in unprocessed form. In yet another embodiment, the dissolution rate of the nanoparticles is at least about 10 times greater than the dissolution rate of the water-insoluble organic pesticide in unprocessed form.

Thus, for example, if one milligram of a water-insoluble organic pesticide requires five minutes to dissolve, only one minute is required for the nanoparticles, at the same concentration. In addition, the solubility (gram material to gram water) also increases upon decreasing the size of the particles In specific embodiments, the water-insoluble organic pesticide is in an amorphous or a partially amorphous form. Amorphous forms may have increased solubility and dissolution rate relative to non-amorphous forms. Using amorphous forms of poorly soluble molecules can be a real advantage. Amorphous materials usually show a significantly higher solubility than their crystalline counterparts, have higher dissolution rate and, in case of drug entities, higher bioavailability in vivo. X-ray diffraction measurements and DSC measurements can be performed on the nanoparticles to reveal the presence of amorphous or crystalline materials.

In one embodiment of the method for preparing a redispersible powder, the process further comprises the step of crystallizing the nanoparticles thereby providing crystalline nanoparticles. In another embodiment, the crystallizing is carried out by aging the nanoparticles. X-ray diffraction measurements can be performed on the nanoparticles to reveal crystallinity.

The invention also provides a pesticide composition comprising as an active agent the redispersible powder of the invention, together with an adjuvant. Adjuvants include wetting agents, crop oil concentrates, spreaders, stickers, preservatives, buffering agents, foaming and anti-foaming agents, dispersing agents and drift control agents.

The present invention also relates to methods for combating insects, mites, fungus and bacteria, comprising applying to the insects, mites, fungus or bacteria an effective amount of the compositions of the invention.

The present invention also relates to methods for protecting crops and upland, including industrial products thereof, such as seeds and fruits, by applying to the crops or products thereof an effective amount of the compositions of the invention.

The composition can be prepared in a variety of forms such as dust, wettable powder, emulsifiable concentrate, inert emulsion, oil solution, aerosol preparation, etc. with adjuvants as the cases of agricultural compositions. The composition can be applied with or without diluting them in suitable concentrations.

Suitable adjuvants include powdery carries such as talc, kaolin, bentonite, diatomaceous earth, silicon dioxide, clay and starch; liquid diluents such as water, xylene, toluene, dimethylsulfoxide, dimethylformamide, acetonitrile, and alcohol; emulsifiers dispersing agents, surfactants such as sodium alkyl benzene sulfonate, polyoxyethylene alkylaryl ether, sodium naphthalene sulfonate formaldehyde condensate, calcium ether sulfate, polyoxyethyleneglycol dodecylphenyl ether, polyoxyethylene lauryl ether, polyoxyethylene fatty acid ester, sodium alkylsulfate, sulfate of polyoxyethylene alkylaryl ether and di-alkylsulfosuccinate etc.

The foregoing description of the specific embodiments will so fully reveal the general nature of the invention that others can, by applying current knowledge, readily modify and/or adapt for various applications such specific embodiments without undue experimentation and without departing from the brand concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

An oil-in-water microemulsion composition was prepared having the indicated percent weight proportions of the following materials: sodium dodecyl sulfate (4%), linear alkyl benzene sulphonate (1.5%), iso-butyl acetate (46%), 2-propanol (22.5%), water (22.5%), novaluron (Rimon®) (2.5%) and Silwet® L-77 (organanosilicone surfactant comprising a blend of polyalkyleneoxide modified heptamethyltrisiloxane and allyloxypolyethylene glycol methyl ether; 1%).

The microemulsion was prepared by first dissolving the required quantity of novaluron in iso-butyl acetate. Next, surfactants and 2-propanol were mixed with water. Aqueous and organic phases were mixed together and vortexed until a transparent microemulsion was formed. Finally, Silwet® L-77 was added and the final microemulsion remained transparent.

The microemulsion was spray dried in a laboratory spray drier. The resulting powder could be stored for months in a sealed vial. The powder was composed of nanoparticles 120 nm in diameter. According to weight it contained sodium dodecyl sulfate (44.4%), linear alkyl benzene sulphonate (16.7%), Silwet® L-77 (11.1%) and novaluron (27.8%). The powder was easily redispersible in water up to 1% according to weight.

Example 2

An oil-in-water microemulsion composition was prepared having the indicated percent weight proportions of the following materials: sodium dodecyl sulfate (6.2%), linear alkyl benzene sulphonate (2.8%), iso-butyl acetate (18.9%), 1-propanol (31.3%), water (39.5%), novaluron (1%), ethyl cellulose (0.1%) and Morwet® (sodium n-butyl naphthalene sulfonate; 0.2%).

The microemulsion was prepared by first dissolving the required quantity of novaluron and ethyl cellulose in iso-butyl acetate. Next, surfactants and 1-propanol were mixed with water. Aqueous and organic phase were mixed together and vortexed until a transparent microemulsion was formed. Finally, Morwet® was added and the final microemulsion remained transparent.

The microemulsion was lyophilized and the resulting powder could be stored for months in a sealed vial. The powder was composed of nanoparticles 210 nm in diameter, and was easily redispersible in water up to 1% according to weight.

Example 3

Nanoparticles of Novaluron Prepared Using Lyophilization and Homogenization

Novaluron (1 g) was dissolved in 19 g of a solution of iso-butyl acetate solution containing ethyl cellulose (10%) to form an organic phase (20 g). Cetyl alcohol was also added. Polyvinyl alcohol (PVA; 2 g) was dissolved in water (78 g). The above ingredients was made into a crude emulsion by treatment with an Ultra Turrax® T 25 for 5 min at 11,000 rpm. The crude emulsion was homogenized at 20,000 psi using a micro fluidizer for two minutes to form a fine dispersion. The homogenized droplets (nanometric in size), were quickly evaporated under vacuum (1 mm Hg at 50 C°). A solution of Morwet®, %) and mannitol (1/1 wt/wt) was added to the dispersion followed by quick freezing using liquid nitrogen and overnight lyophilization. The resulting fluffy powder contained novaluron up to 45% according to weight, and was easily dispersible in water, without any requirement for a means of dispersal such as stirring apparatus or ultrasonication. The resulting dispersion contained nanoparticles of less then 300 nm mean diameter.

Example 4

Nanoparticles of Novaluron Prepared Using Morewet® as Both Emulsifier and Wetting Agent Novaluron (1.5 g) was dissolved in isobutyl acetate (28.5 g). The solution was emulsified in 70 g aqueous solution of Morwet® (1 g in 70 ml). The full procedure of high pressure homogenization and solvent evaporation was applied. The crude emulsion was prepared by 5 minutes homogenization by ultra turrax, followed by homogenization at 10,000 psi using a high pressure homogenizer (Stansted FPG7400) for one pass. The homogenized emulsion (nanometric in size), was quickly evaporated under vacuum (1 mm Hg at 50 C°) yields a solvent-free dispersion of 180 nm particles. When mixing the dispersion with Morwet® solution (5% w/w) on a stirrer, and lyophilizing the overall dispersion, a powder is obtained with novaluron concentration of 20% according to weight. Redispersion of the powder yielded particles 250 nm in diameter with no means of mechanical energy input but manual shaking. A DSC (differential scanning calorimetry) analysis demonstrated a low crystalline content of the active agent, suggesting that the insecticide was mostly in an amorphous state.

Example 5

Nanoparticles of Novaluron Prepared Using Spray-Dryer

Novaluron (0.5 g) was dissolved in a solution of isobutyl acetate containing ethyl cellulose (2%). Then it was emulsified in an aqueous solution of 2% polyvinyl pyrrolidone (30,000-70,000 MW). The emulsion was homogenized in a high pressure homogenizer, first at low pressure of 5000 psi and then with two additional cycles of 15,000 psi. The aqueous dispersion contained particles of diameter 300 nm. Upon drying in a spray-dryer, a powder having novaluron content up to 4% according to weight was obtained.

Example 6

An oil-in-water microemulsion composition was prepared having the indicated percent weight proportions of the following materials: sodium dodecyl sulfate (4%), linear alkyl benzene sulphonate (1.5%), iso-butyl acetate (47%), 2-propanol (22%), water (22%), novaluron (Rimon®) (2.5%) and Morwet® D 485 (sodium n-butyl naphthalene sulfonate surfactant; 1%).

The microemulsion was prepared by first dissolving the required quantity of novaluron in iso-butyl acetate. Next, surfactants and 2-propanol were mixed with water. Aqueous and organic phases were mixed together and vortexed until a transparent microemulsion was formed. Finally, Morwet® was added and the final microemulsion remained transparent.

The microemulsion was spray dried in a laboratory spray drier. The resulting powder could be stored for months in a sealed vial. The powder was composed of nanoparticles 120 nm in diameter. According to weight it contained sodium dodecyl sulfate (44.4%), linear alkyl benzene sulphonate (16.7%), Morwet® (11.1%) and novaluron (27.8%). The powder was easily redispersible in water up to 1% according to weight.

Example 7

An oil-in-water microemulsion composition was prepared having the indicated percent weight proportions of the following materials: sodium dodecyl sulfate (5%), linear alkyl benzene sulphonate (1.5%), iso-butyl acetate (25%), 2-propanol (22.4%), water (42.5%), novaluron (Rimon®; (2.6%) and Morwet® (sodium n-butyl naphthalene sulfonate surfactant; 1%).

The microemulsion was prepared by first dissolving the required quantity of novaluron in iso-butyl acetate. Next, surfactants and 2-propanol were mixed with water. Aqueous and organic phase were mixed together, warmed to 55° C. and vortexed until a transparent microemulsion was formed. Finally, Morwet® was added and the final microemulsion remained transparent. The microemulsion showed high electrical conductivity, implying oil-in-water character.

The microemulsion was lyophilized and the resulting powder was composed of nanoparticles 240 nm in diameter, and was easily redispersible in water up to 1% according to weight.

Example 8

Novaluron preparations were prepared as in Example 4 (R-M-1) and Example 6 (SR-2605-1) (by high pressure homogenization). Cotton leaves were treated with the formulation R-M-1 or with n conventional emulsifiable concentrate (EC) formulation (0.2 mg a.i./liter) and then were exposed to $1^{st}$-instar S. littoralis for 3-day feeding. The larvae were fed for an additional 3 days on untreated leaves. Mortality was determined after 3 and 6 days. The results, shown in Table 1, indicate that the nanoparticle formulations R-M-1 and SR-2605-1, are each considerably more potent than the EC formulation.

TABLE 1

Effect of novaluron formulations on S. littoralis $1^{st}$ instars

| Formulation and concentration at mg a.i./liter | No of $L_1$ | Mortality, % ± SEM after | |
|---|---|---|---|
| | | 3 d | 6 d |
| 0 (Control) | 50 | 0 a | 0 a |
| EC-10 (50110862) | 50 | 6 ± 3 b | 46 ± 8 bc |
| R-M-1 (20%) | 50 | 10 ± 5 b | 92 ± 4 d |
| SR-2605-1 (28 WT %) | 50 | 12 ± 5 b | 72 ± 15 cd |

Data are averages ± SEM of 5 replicates 10 larvae each. Means followed by the same letter do not differ significantly at P = 0.05.

Example 9

Novaluron preparations SR-2605-1 was prepared as in Example 6, and R-M-1 was prepared as in Example 4

Cotton plants were treated with the formulations at a concentration 0.8 mg a.i./litre. The treated leaves were collected periodically and exposed for 3-day feeding to $1^{st}$-instars S. littoralis and for an additional 3 days on untreated leaves. Mortality was determined after 6 days. The results, shown in Table 2, indicate that the residual activity of R-M-1 and SR-2601-1 were both considerably more prolonged than that of EC-10. At day 14, R-M-1 and SR-2605-1 resulted in 62% and 64% mortality respectively, while EC-10 resulted in 12% mortality.

TABLE 2

Potency and residual activity of cotton seedlings treated with various novaluron formulations on $1^{st}$-instars Spodoptera littoralis

| | Percent of larval mortality at various days after application Formulation | | | | | | | |
|---|---|---|---|---|---|---|---|---|
| | 0 | 7 | 14 | 21 | 28 | 35 | 42 | 57 |
| Control | 0 a | 0 a | 4 ± 3 a | 6 ± 4 a | 2 ± 2 a | 4 ± 3 a | 0 a | 2 ± 2 a |
| EC-10 (50110862) | 80 ± 3 b | 55 ± 13 b | 12 ± 2 b | 16 ± 8 ab | 16 ± 5 b | 14 ± 8 ab | 14 ± 3 b | 14 ± 3 b |
| SR-2605-1 (28 wt %) | 100 c | 65 ± 13 b | 64 ± 8 c | 26 ± 4 b | 24 ± 7 bc | 22 ± 8 b | 22 ± 6 b | 24 ± 3 c |
| R-M-1 (20%) | 100 c | 90 ± 3 c | 62 ± 7 c | 62 ± 8 c | 58 ± 11 c | 58 ± 10 c | 36 ± 17 bc | 20 ± 12 abc |

Data are averages ± SEM of 5 replicates of 10 larvae each. Means followed by the same letter do not differ significantly at P = 0.05.

Example 10

Nanoparticles of Lambda-Cyhalothrin Prepared Using High Pressure Homogenization/Solvent Evaporation Lambda-cyhalothrin (5 g) was dissolved in a solution of toluene (15 g) containing ethyl cellulose (10%) to form an organic phase (20 g). Atlox® 4913 (an ABA block copolymer surfactant comprising polyethylene oxide and poly 12-hydroxystearic acid; 3 g) and lauryl sulfate (0.1 g) were dissolved in water. The solutions were mixed and made into a crude emulsion by treatment with an ultaturrax-T25 for 10 min at 10,000 rpm. The crude emulsion was homogenized at 10,000 psi using a Stansted FPG7400 high-pressure single stage homogenizer for two passes to form a fine emulsion containing nanometric size droplets. The dispersion was quickly evaporated under vacuum of 1 mmHg 42 C°. The resulting dispersion was analyzed by light scattering (FIG. 1), which revealed lambda-cyhalothrin particles with a 220 nm mean diameter. The dispersion was stable for well over a month. Comparison of the obtained dispersion and a conventional emulsifiable concentrate formulation showed similar effects in a biological assay of adult mortality of *Bemisia tabaci* (Table 3).

TABLE 3

Biological assay of adult mortality of *Bemisia tabaci*

| Formulation | Biological parameters | | | |
|---|---|---|---|---|
| | n | Slope | $LC_{50}$ | $LC_{90}$ |
| 5 EC (#040201) | 579 | 1.28 ± 0.13 | 0.6 (0.4-0.8) | 6 (4-9) |
| 6 SC (cump) | 694 | 1.33 ± 0.10 | 3 (1-4) | 23 (13-65) |

Example 11

A dispersion similar to that described in Example 10 was prepared, using only SDS as surfactant. Mixing the resulting dispersion with a second dispersion of Aerosil® 200 (with particles in the region of ~30 nm) followed by lyophilization overnight resulted in a fluffy powder with lambda-cyhalothrin content of 33% according to weight. Redispersal in water required only manual agitation, and yielded nanometric particles up to 250 nt in diameter.

The contents of all the references mentioned throughout the specification are hereby expressly incorporated by reference in their entirety, as if fully set forth herein.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A process for preparing a pesticide composition, which comprises:
    (i) forming an oil-in-water emulsion by combining a water-insoluble organic pesticide, a volatile water-immiscible organic solvent, water and at least one surfactant, wherein the emulsion is a thermodynamically stable microemulsion that has a droplet size of less than about 30 nm and that is formed spontaneously without the use of high-pressure homogenizer or a high shear instrument; or wherein the emulsion is a nanoemulsion having a droplet size of less than about 300 nm formed by combining a water-insoluble organic pesticide, a volatile water-immiscible organic solvent, water and at least one surfactant using a high pressure homogenizer or a high shear instrument; and (ii) removing the volatile water-immiscible organic solvent and the water from the nanoemulsion or microemulsion in one step to form a pesticide composition in the form of a dispersible powder comprising nanoparticles having a diameter of about 5 to about 300 nm;
    wherein the nanoparticles are in finely divided particulate form to impart a solubility that is substantially greater than that of the pesticide in a conventional emulsifiable concentrate formulation.

2. The process according to claim 1, wherein the oil-in-water emulsion is a microemulsion having a droplet size of less than about 30 nm and the dispersible powder that is formed comprises nanoparticles having a diameter of about 5 to about 30 nm.

3. The process according to claim 1, wherein the oil-in-water emulsion is a nanoemulsion having a droplet size of less than about 300 nm and the dispersible powder that is formed comprises nanoparticles having a diameter of about 5 to about 300 nm.

4. The process according to claim 1, wherein the step of preparing the oil-in-water microemulsion or nanoemulsion comprises:
    (i) dissolving the water-insoluble organic pesticide in the volatile water-immiscible organic solvent so as to form an organic phase; and
    (ii) mixing the organic phase with water and a surfactant to form the oil-in-water emulsion.

5. The process according to claim 1, wherein the volatile water-immiscible organic solvent and water are removed by spray drying or lyophilization.

6. The process according to claim 1, further comprising the step of redispersing the pesticide powder in water to form an aqueous dispersion of pesticide nanoparticles.

7. The process according to claim 1, wherein the water-insoluble organic pesticide is selected from the group consisting of an insecticide, a herbicide, a fungicide, an acaricide, an algicide, an antimicrobial agent, biopesticide, a biocide, a disinfectant, a fumigant, an insect growth regulator, a plant growth regulator, a miticide, a microbial pesticide, a molluscide, a nematicide, an ovicide, a pheromone, a repellent, a rodenticide, a defoliant, a dessicant and mixtures thereof.

8. The process according to claim 7, wherein the water-insoluble organic pesticide is novaluron or lambda-cyhalothrin.

9. The process according to claim 7, wherein the water-insoluble organic pesticide is an insecticide, herbicide or fungicidally active compound, and further wherein:
    the insecticide is selected from the group consisting of a benzoyl urea, novaluron, lufenuron, chlorfluazuron, flufenoxuron, hexaflumuron, noviflumuron, teflubenzuron, triflumuron, diflubenzuron; a carbamate, a pyrethroid, cyhalothrin and isomers thereof, lambda-cyhalothrin, deltamethrin, tau-fluvalinate, cyfluthrin, beta-cyfluthrin, tefluthrin, bifenthrin; an organophosphate, azinfos-methyl, chlorpyrifos, diazinon, endosulfan, methidathion; a neonicotinoid, a phenylpyrazole, imidacloprid, acetamiprid, thiacloprid, dinotefuran, thiamethoxam and fipronil;
    the fungicidally active compound is selected from the group consisting of a conazole, epoxiconazole, hexaconazole, propiconazole, prochloraz, imazalil, triadimenol, difenoconazole, myclobutanil, prothioconazole, triticonazole, tebuconazole, a morpholine, dimethomorph, fenpropidine fenpropimorph, a strobilurin, azoxystrobin, kresoxim-methyl, phthalonitriles, chlorothalonil; mancozeb; fluazinam; a pyrimidine and bupirimate; and
    the herbicide is selected from the group consisting of an aryloxyphenoxy derivative, an aryl urea, an aryl carboxylic acid, an aryloxy alkanoic acid, clodinafop-propargyl, fenoxaprop-pethyl, propaquizafop, quizalafop, a dintroaniline, pendimethalin, trifluralin; a diphenyl ether, oxyfluorfen, an imidazolinone, a sulfonylurea, chlorsulfuron, nicosulfuron, rimsulfuron, tribenuron-methyl, a sulfonamide, a triazine, a triazinone and metamitron.

10. The process according to claim 1, wherein the volatile water-immiscible organic solvent is selected from the group consisting of n-butyl acetate, sec-butyl acetate, isobutyl acetate, propyl acetate, amyl acetate, toluene, xylenes, R(+)-limonene, hexane, pentane, heptane, cyclohexane and mixtures thereof.

11. The process according to claim 1, wherein the microemulsion or nanoemulsion further comprises at least one polymer wherein:
- the polymer is a water insoluble polymer selected from the group consisting of polylactic acid, cellulose acetate, methyl cellulose, ethyl cellulose, hydroxylpropyl methyl cellulose, poly(lactic-co-glycolic acid), hydroxylpropyl cellulose phthalate, and mixtures thereof; or
- the polymer is a water soluble polymer selected from the group consisting of polyvinyl pyrrolidone (PVP), polyvinyl alcohol, carboxy methyl cellulose, hydroxy ethyl cellulose, polyethylene glycol, and mixtures thereof; or
- the polymer is a non-crosslinked polymer; and
- the polymer is present in an amount of about 0.01 to about 10% by weight based on the total weight of the emulsion.

12. The process according to claim 1, wherein the microemulsion or nanoemulsion further comprises a re-dispersion aid which is selected from the group consisting of a wetting agent, a disintegrant, a water soluble polymer, colloidal silica particles, sugars, mannitol and mixtures thereof; or
- wherein the microemulsion or nanoemulsion further comprises a co-solvent.

13. The process according to claim 1, wherein the at least one surfactant is selected from the group consisting of a cationic surfactant, an anionic surfactant, an amphoteric surfactant, a nonionic surfactant and mixtures thereof, and further wherein:
- the anionic surfactant is selected from the group consisting of an alkyl benzene sulphonate, condensate sodium salts, sodium dodecyl sulfate, sodium sulfosuccinate, sodium lauryl sulfate, sodium stearate, sodium alkyl naphthalene sulfonate and mixtures thereof;
- the nonionic surfactant is selected from the group consisting of an ethoxylated sorbitan ester, a sorbitan ester, an organosilicone surfactant, a polyglycerol ester, a sucrose ester, a poloxamer, an alkyl polyglucoside, polyalkyleneoxide modified heptamethyltrisiloxanes, and allyloxypolyethylene glycol methylether and mixtures thereof; or
- the amphoteric surfactant is lecithin; or
- the cationic surfactant is selected from the group consisting of cetyl trimethyl ammonium bromide, cetyl trimethyl ammonium chloride, and mixtures thereof;
- or wherein the surfactant is sodium n-butyl naphthalene sulfonate or an organosilicone surfactant comprising a blend of polyalkyleneoxide modified heptamethyltrisiloxane and allyloxypolyethylene glycol methyl ether.

14. The process according to claim 1, wherein the water-insoluble organic pesticide is in an amorphous or a partially amorphous form.

15. The process according to claim 1, further comprising combining said dispersible pesticide with an acceptable adjuvant.

16. The process according to claim 1, wherein the nanoparticles comprise at least about 80% by weight of the water-insoluble organic pesticide.

17. The process according to claim 1, wherein the dispersible powder further comprises at least one polymer.

18. The process according to claim 1, further comprising the step of crystallizing the nanoparticles, thereby providing crystalline organic nanoparticles.

19. A process for preparing a pesticide composition, which comprises:
(i) forming an oil-in-water emulsion by combining a water-insoluble organic pesticide, a volatile water-immiscible organic solvent, water and at least one surfactant, wherein the emulsion is a thermodynamically stable microemulsion that has a droplet size of less than about 30 nm and that is formed spontaneously without the use of high-pressure homogenizer or a high shear instrument; and (ii) removing the volatile water-immiscible organic solvent and the water from the nanoemulsion or microemulsion in one step to form a pesticide composition in the form of a dispersible powder comprising nanoparticles having a diameter of about 5 to about 30 nm;
wherein the nanoparticles are in finely divided particulate form to impart a solubility that is substantially greater than that of the pesticide in a conventional emulsifiable concentrate formulation.

20. A process for preparing a pesticide composition, which comprises:
(i) forming an oil-in-water nanoemulsion having a droplet size of less than about 300 nm by combining a water-insoluble organic pesticide, a volatile water-immiscible organic solvent, water and at least one surfactant using a high pressure homogenizer or a high shear instrument; and (ii) removing the volatile water-immiscible organic solvent and the water from the nanoemulsion or microemulsion in one step to form a pesticide composition in the form of a dispersible powder comprising nanoparticles having a diameter of about 5 to about 300 nm;
wherein the nanoparticles are in finely divided particulate form to impart a solubility that is substantially greater than that of the pesticide in a conventional emulsifiable concentrate formulation.

* * * * *